(12) United States Patent
Knowlton

(10) Patent No.: US 6,241,753 B1
(45) Date of Patent: *Jun. 5, 2001

(54) METHOD FOR SCAR COLLAGEN FORMATION AND CONTRACTION

(75) Inventor: Edward W. Knowlton, Danville, CA (US)

(73) Assignee: Thermage, Inc., Hayward, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/583,815

(22) Filed: Jan. 5, 1996

Related U.S. Application Data

(63) Continuation-in-part of application No. 08/435,822, filed on May 5, 1995, now Pat. No. 5,755,753.

(51) Int. Cl.[7] ............................................. A61F 7/00
(52) U.S. Cl. .......................... 607/99; 128/898; 607/96; 607/97; 607/98; 607/99; 607/100; 607/101; 607/102; 607/103; 607/104; 607/105; 600/21; 600/22; 600/23; 600/24; 600/25; 600/26; 600/27; 600/28
(58) Field of Search ..................... 128/898; 606/27–34, 606/40–52; 607/96–105, 108–114

(56) References Cited

U.S. PATENT DOCUMENTS

| | | |
|---|---|---|
| Re. 32,849 | 1/1989 | Wei et al. . |
| 3,831,604 | 8/1974 | Neefe . |
| 4,074,718 | 2/1978 | Morrison . |
| 4,140,130 | 2/1979 | Storm, III . |
| 4,164,226 | 8/1979 | Tapper . |

(List continued on next page.)

FOREIGN PATENT DOCUMENTS

| | | |
|---|---|---|
| 1 949 534 | 4/1970 | (DE) . |
| 31 21 683 | 12/1982 | (DE) . |
| 0 519 415 | 12/1992 | (EP) . |
| 2 609 245 | 7/1988 | (FR) . |
| 266678 | 12/1997 | (NZ) . |

(List continued on next page.)

OTHER PUBLICATIONS

Adrian, R. M. Treatment of Facial Telangiectasia Using the VersaPulse® Variable Pulse Width Frequency Doubled Neodymium: YAG Laser: A Case Report.

Chess, C.; Chess, Q. "Cool Laser Optics Treatment of Large Telagiestasia of the Lower Extremities."*J. Dermatol Surg Oncol.* 1993; 19:74–80.

(List continued on next page.)

*Primary Examiner*—David M. Shay
(74) *Attorney, Agent, or Firm*—Wilson Sonsini Goodrich & Rosati

(57) ABSTRACT

A method is disclosed for forming and contracting scar collagen below a tissue surface in a selected tissue site. An electromagnetic energy apparatus is provided and includes an electromagnetic energy source and a delivery device. The delivery device is positioned on the tissue surface. Electromagnetic energy is produced from the electromagnetic energy source and delivered through the tissue surface to the selected tissue site for a sufficient time to induce scar collagen formation in the selected tissue site. No more than a second degree burn is formed on the tissue surface. The scar collagen is then contracted. This method is particularly useful in tissue sites that are devoid or deficient in collagen.

23 Claims, 6 Drawing Sheets

U.S. PATENT DOCUMENTS

| | | |
|---|---|---|
| 4,290,435 | 9/1981 | Waggott . |
| 4,343,301 | 8/1982 | Indech . |
| 4,346,715 | 8/1982 | Gammell . |
| 4,375,220 | 3/1983 | Matvias . |
| 4,381,007 * | 4/1983 | Doss .................................... 606/5 |
| 4,441,486 | 4/1984 | Pounds . |
| 4,545,368 | 10/1985 | Rand et al. . |
| 4,676,258 | 6/1987 | Inokuchi et al. . |
| 4,709,701 | 12/1987 | Weber . |
| 4,881,543 | 11/1989 | Trembly et al. . |
| 4,887,614 | 12/1989 | Shirakami et al. . |
| 4,889,122 | 12/1989 | Watmough et al. . |
| 4,944,302 | 7/1990 | Hernandez et al. . |
| 4,957,480 | 9/1990 | Morenings ........................ 604/20 |
| 4,962,761 | 10/1990 | Golden ............................ 128/400 |
| 4,976,709 | 12/1990 | Sand .................................. 606/5 |
| 5,003,991 | 4/1991 | Takayama et al. ............. 128/784 |
| 5,133,351 | 7/1992 | Masaki ........................ 128/419 R |
| 5,143,063 | 9/1992 | Fellner ............................ 128/399 |
| 5,186,181 | 2/1993 | Franconi et al. ............... 128/804 |
| 5,190,517 | 3/1993 | Zieve et al. ..................... 604/22 |
| 5,230,334 | 7/1993 | Klopotek ........................ 128/399 |
| 5,249,575 | 10/1993 | DiMino et al. ................. 607/150 |
| 5,282,797 | 2/1994 | Chess . |
| 5,304,169 | 4/1994 | Sand .................................. 606/5 |
| 5,315,994 | 5/1994 | Guibert et al. .................. 607/101 |
| 5,334,193 | 8/1994 | Nardella . |
| 5,342,357 | 8/1994 | Nardella . |
| 5,348,554 | 9/1994 | Imran et al. . |
| 5,366,443 | 11/1994 | Eggers et al. . |
| 5,370,642 | 12/1994 | Keller ................................ 606/9 |
| 5,374,265 | 12/1994 | Sand .................................. 606/5 |
| 5,423,807 | 6/1995 | Milder ............................. 606/20 |
| 5,423,811 | 6/1995 | Imran et al. . |
| 5,437,662 | 8/1995 | Nardella . |
| 5,458,596 * | 10/1995 | Lax et al. ........................ 606/31 |
| 5,462,521 | 10/1995 | Brucker et al. ................. 604/20 |
| 5,464,436 | 11/1995 | Smith . |
| 5,496,312 | 3/1996 | Klicek . |
| 5,507,790 | 4/1996 | Weiss . |
| 5,569,242 | 10/1996 | Lax et al. . |
| 5,681,282 | 10/1997 | Eggers et al. . |
| 5,683,366 | 11/1997 | Eggers et al. . |
| 5,692,058 | 11/1997 | Eggers et al. . |
| 5,693,045 | 12/1997 | Eggers . |
| 5,697,281 | 12/1997 | Eggers et al. . |
| 5,697,536 | 12/1997 | Eggers et al. . |
| 5,697,882 | 12/1997 | Eggers et al. . |
| 5,697,909 | 12/1997 | Eggers et al. . |

FOREIGN PATENT DOCUMENTS

| | | |
|---|---|---|
| WO 92/19414 | 11/1992 | (WO) . |
| 93/13816 | 7/1993 | (WO) . |
| 94/26228 | 11/1994 | (WO) . |
| 96/27240 | 9/1996 | (WO) . |
| 96/27327 | 9/1996 | (WO) . |
| 96/32051 | 10/1996 | (WO) . |
| 96/34568 | 11/1996 | (WO) . |
| 96/39914 | 12/1996 | (WO) . |
| 97/18765 | 5/1997 | (WO) . |
| 97/18768 | 5/1997 | (WO) . |
| 98/03117 | 1/1998 | (WO) . |
| 98/03220 | 1/1998 | (WO) . |

OTHER PUBLICATIONS

Coulson, W. F. et al. "Nonablative Laser Treatment of Facial Rhytides: Animal Study." Abstract for BiOS '98 Symposium Conference: bo05—Cutaneous Applications of Lasers, Jan. 24–30, 1998, San Jose, CA.

Kincade, K. "Demand for Laser Resurfacing Soars: Quicker Healing, Less Risk of Scarring" *Dermatology Times*. 1995. 16(10).

Fitzpatrick, R. "Treatment of Wrinkles with the UltraPulse $CO_2$ Laser.".

Laser Aesthetics, Inc. "The Cool Touch Laser." Brochure.

Laser Aesthetics, Inc. "Cool Touch Model 130 Technical Specifications." Brochure.

National Health Communications, Inc. "New Laser Eliminates 'Lipstick Bleed'" Press Release Jul. 1993.

Allain, et al. "Isometric Tensions Developed During the Hydrothermal Swelling of Rat Skin", Connective Tissue Research, vol. 7, pp. 127–133, (1990).

Danielson, C. "Age–Related thermal stability and susceptibility to proteolysis of rat bone collagen", . . . chem, Great Britain, pp. 697–701, (1990).

Danielson, C. "Thermal stability of reconstituted collagin fibrils, shrinkage characteristics upon in vitro maturation", Mechanisms of Ageing and Development, vol 15, pp. 269–278, (1981).

Kronick, et al. "The locations of collagens with different thermal stabilities in fibrils of bovine recticular dermis". Connective Tissue Research, vol. 18, pp. 123–134, (1988).

Mainster, M.A. "Ophthalmic applications of infrared lasers—thermal considerations", Visual Sci., pp. 414–420, Apr. 1979.

Pearce, et al. "Kinetic models of laser–tissue fusion processes", ISA, paper #93–044, pp. 355–360, (1993).

* cited by examiner

METHOD FOR SCAR COLLAGEN FORMATION AND CONTRACTION

CROSS-REFERENCE TO RELATED CASES

The present application is a continuation-on-part of U.S. patent application Ser. No. 08/435,822, filed May 5, 1995 now U.S. Pat. No. 5,755,753, issued on May 26, 1998, entitled "Method and Apparatus for Controlled Contraction of Collagen Tissue", having the same named inventor Edward W. Knowlton, incorporated herein by reference.

BACKGROUND OF THE INVENTION

1. Field of the Invention

This invention relates generally to a method for creating scar collagen, and more particularly to a method for initiating the formation and healing of scar collagen or bony callus, and subsequently remodelling the scar collagen or bony callus.

2. Description of Related Art

The skin is composed of two basic elements, the epidermis and the underlying dermis. The underlying dermis provides the main structural support of the skin. The epidermis contains the epithelial cells and pigment forming cells called melanocytes. The dermis varies in thickness throughout the body. For instance, the skin is 25 times thicker on the back than on the eyelid.

The dermis is composed mainly of an extracellular protein called collagen. Collagen exists as a triple helix with three polypeptide chains that are connected with heat labile and heat stable chemical bonds. When collagen is heated, alterations in the physical properties of this protein occur at a characteristic temperature. This structural transition occurs at a specific shrinkage temperature.

The phenomenon of thermal shrinkage of collagen begins with a denaturization of the triple helix of the collagen molecule. Thermal energy severs the heat labile bonds that stabilize the triple stranded helix. As a result, the longitudinal axis of the molecule contracts. Partial denaturization of collagen tissue occurs in second degree burns and is typically applied as a standard thermal gradient that is hotter on the surface and cooler in the underlying dermis. In burn patients, partial denaturization of dermal collagen provides a tightening effect on the skin. By applying a reverse thermal gradient which cools the surface of the skin while heating the underlying collagen-containing layers, contraction of collagen in the absence of a second degree burn (and its inherent blistering and pigmentary irregularities) is possible. Because collagen is found in tendon, bone, cartilage and all other connective tissue throughout the body, reverse thermal gradient contraction of collagen can have many applications.

The selective induction of the basic wound healing process serves as the basis for the second major application of thermal shrinkage of collagen. In higher developed animal species, the wound healing response to injury involves an initial inflammatory process that subsequently leads to the deposition of scar tissue. The initial inflammatory response consists of the infiltration by white blood cells or leukocytes that dispose of cellular debris. Forty-eight hours later, proliferation of fibroblasts at the injured site occurs. These cells then produce scar collagen that functions as the main support structure of a healed wound. The deposition and subsequent remodeling of this nascent scar collagen provides the means to alter the consistency and geometry of soft tissue for both aesthetic and reconstructive purposes.

There exists an aesthetic need to contract skin without the scars, surgical risks or pigmentary side effects of commonly employed technique. These techniques include surgical resection of skin and the use of lasers and chemical peels to achieve a tighter, more youthful skin appearance. Understandably, many patients are hesitant to subject themselves to these procedures, even though an overall aesthetic improvement is likely.

Skin resection procedures are limited in their application due to inherent scars. With face-lift procedures, scars can be hidden around the contour of the ear, thus providing an acceptable trade-off between the surgical scar and the aesthetic improvement. Surgical resection of skin on the hips, thighs, arms, knees and legs, however, provides only a modest improvement with fairly unsightly scarring. In addition, patients must undergo a post-operative phase of healing that may be both painful and inconvenient. Other risk factors, such as bleeding and infection, may prolong healing.

Liposuction is effective at removing fat in some areas, however, it does not tighten the skin envelope. Skin resurfacing techniques that secondarily tighten excess skin (such as laser and chemical peels) employ a standard thermal gradient that requires burning off the superficial skin as a second degree burn. The thermal effects of collagen contraction in the deeper dermis occur, but require a painful healing phase due to the second degree burn. These modalities depend upon reepithelialization with cell migration from the skin appendages. This process of reepithelialization is similar to the healing of any thermal burn and is more likely to cause pigmentary irregularities due to the destruction of melanocytes in the epidermis.

Adipose tissue, more commonly known as fat, is formed of cells containing stored lipid. Adipose tissue is often subdivided into small loculations by connective collagen tissue serving as the fibrous septae.

There exists a need for subcutaneously contracting of collagen without surgical scarring or pigmentary side effects of more invasive techniques. There is a further need for subcutaneously inducing the formation and contraction of scar collagen in a selected tissue site while creating no deeper than a second degree burn on the surface of the selected tissue site.

SUMMARY OF THE INVENTION

It is an object of the present invention to provide a method for thermal remodelling and contraction of collagen without surgical scarring or pigmentary side effects.

Another object of the present invention is to provide a method for inducing the formation and contraction of scar collagen.

A further object of the present invention is to provide a method for inducing the formation and contraction of scar collagen in a selected tissue site while creating no deeper than a second degree burn on the surface of the selected tissue site.

Yet another object of the present invention is to provide a method for inducing the formation and contraction of bony callus in periosteum tissue.

Still a further object of the present invention is to provide a method for contracting collagen tissue no deeper than a second degree burn formed on a tissue surface overlying the contracted collagen tissue, and preferably no deeper than a first degree burn.

These and other objects of the invention are provided in a method for forming and contracting scar collagen below a tissue surface in a selected tissue site. An electromagnetic energy apparatus is provided and includes an electromagnetic energy source and a delivery device. The delivery device is positioned on the tissue surface. Electromagnetic energy is produced from the electromagnetic energy source and delivered through the tissue surface to the selected tissue site for a sufficient time to induce scar collagen formation in the selected tissue site. No deeper than a second degree burn is formed on the tissue surface. The scar collagen is then contracted. This method is particularly useful in soft tissue sites that are devoid or deficient in collagen.

In another embodiment, a method is disclosed for forming callus deposition in a selected periosteum tissue site. An electromagnetic energy apparatus is provided and includes an electromagnetic energy source and a delivery device. The delivery device is positioned on a tissue surface of the selected periosteum tissue site. Electromagnetic energy is produced from the electromagnetic energy source. Electromagnetic energy is transcutaneously delivered from the delivery device, through the tissue surface, and to the selected periosteum tissue site for a sufficient time to induce callus formation in the selected periosteum tissue site. After scar collagen formation the callus is then contracted.

Suitable applications for the methods of the present invention include but are not limited to, tightening and firming soft tissue, unstable joints due to collateral ligament laxity, the treatment of unstable spinal column disorders, treatment of weaknesses of the abdominal wall, treatment of other connective tissues, esophageal hernia with reflux, urinary incontinence in women, dysdynamic segments of the myrocardium and other aneurysmal dilatations of the vessel, sleep apnea, laxity and wrinkling of the skin, and the like.

Wrinkling of the skin occurs as a consequence of inadequate support of the epidermis. The induction of scar collagen deposition is used for the treatment of wrinkles. Improved skin turgor is accomplished by first replenishing the collagen matrix that has been lost with aging. Following the deposition of nascent scar collagen in the dermis, contraction of collagen with a reverse thermal gradient corrects wrinkling of the skin without resorting to resurfacing techniques that require the application of a standard thermal gradient burn to the skin. This is achieved without undergoing a lengthy post-operative healing process. Bleeding and infection is reduced. Second degree burns to the superficial skin are minimized. The melanocytes are not damaged and pigmentary irregularities are avoided.

One apparatus used to create the reverse thermal gradient is a combined heating pad that has both cooling elements and electromagnetic delivery devices. The heating pad is configured to the topography of the treatment area and is incorporated into an elastic garment. Partial denaturization of collagen with contraction of skin is achieved with each treatment. Thermal transducers measure the surface temperature of the treatment area to avoid blistering. In one embodiment the deeper dermis is heated to above 65 degrees for collagen contraction. The temperature can vary depending on local tissue factors. Sequential treatments are designed to allow for more precision of the end result. Areas of application are not confined by requirements to either hide surgical incisions or transition along aesthetic boundaries.

Because scarring and pigmentary irregularities are avoided, skin or other tightening occurs in areas previously considered "off-limits" to standard methods of surgical resection, laser and chemical resurfacing. Skin tightening with a reverse thermal gradient contraction of collagen can correct areas including but not limited to the thighs, knees, arms, back and hips without unsightly scarring of standard techniques. In addition, areas previously corrected by aesthetic procedures, such as face and neck lifts, can be corrected without requiring surgery or the typical incisions around the ear. Elastosis or stretching of the abdominal skin from pregnancy can be corrected without the extensive incision of an abdominoplasty. The method of the present invention can also be used for mastopexies or breast uplifts.

The fibrous septae in subcutaneous fat layers can be contracted to tighten the soft tissue. Along with the extracellular effects of collagen, intracellular effects upon the fat cell, or lipocyte, by thermal induction cause a net reduction of fat in the lipocyte which achieves a net reduction in volume of the treated area. A second thermal device is used in tandem with the initial thermal device to achieve liposculpture of the treated area. The second device can be designed with a convergent lens that is focused at the appropriate level on the subcutaneous tissue.

A variety of electromagnetic energy sources can be employed. Suitable energy sources include but are not limited to RF, microwave, ultrasound and the like. In one embodiment, the preferred energy source is RF.

DETAILED DESCRIPTION

Figure 1:
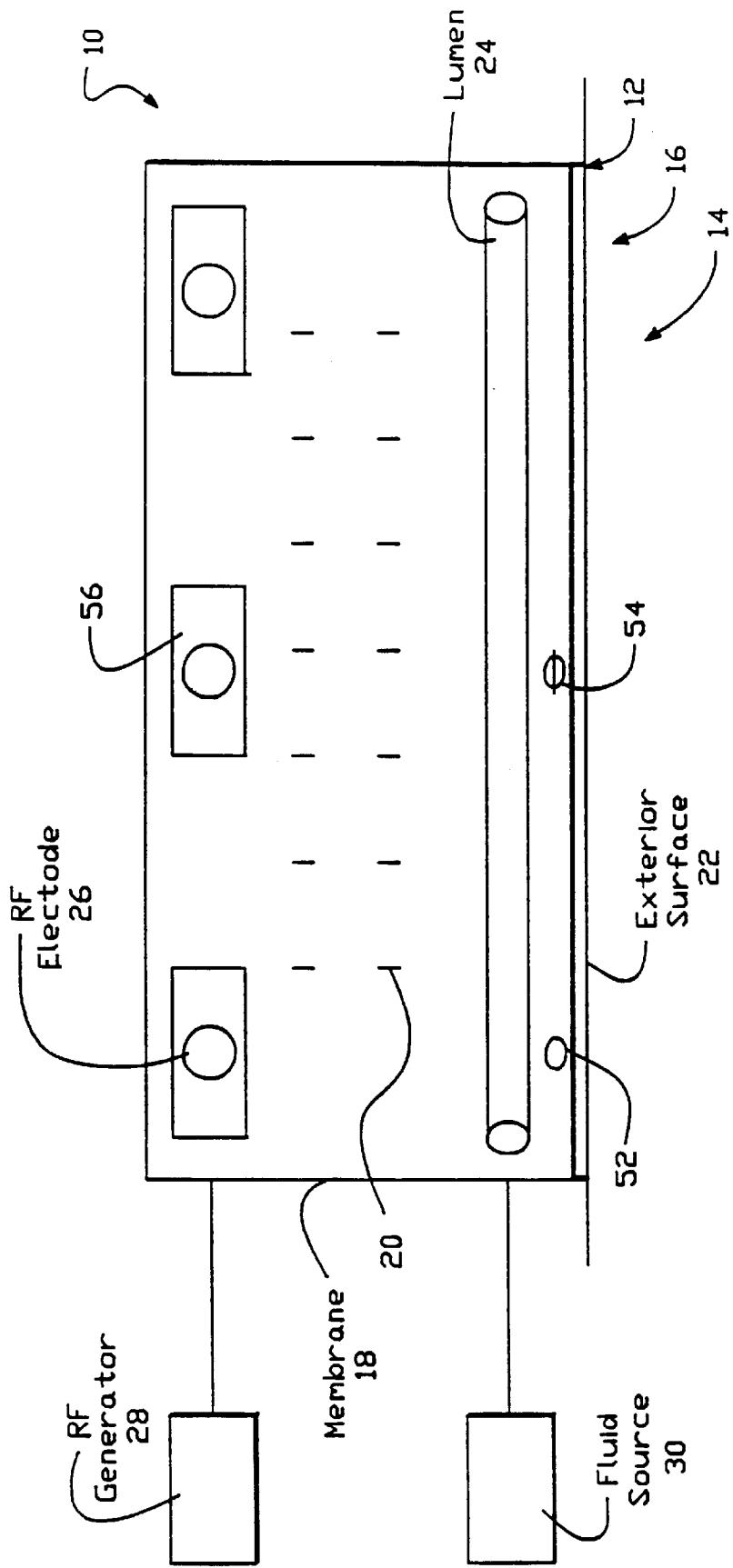
FIG. 1 is a perspective view of an apparatus for applying electromagnetic energy through the skin in order to cause a partial denaturization of collagen tissue, resulting in a tightening of the skin.

For purposes of this specification, the following definitions apply.

Pre-existing collagen is the protein substance normally present in the white fibers (collagenous fibers) of skin, tendon, bone cartilage and all other connective tissue.

Thermal induction of scar collagen deposition is a nonablative neosynthetic process of collagen deposition as a reaction to inflammation induced by thermal injury. The resulting scar collagen is frequently referred to as nascent, as opposed to pre-existing.

Standard thermal gradient is the thermal content of tissue that is greater on the skin surface.

Reverse thermal gradient is, (i) the application of electromagnetic energy to alter the biophysical properties of collagen, i.e., contraction, with minimal blistering of the tissue surface, (ii) a gradient in which the tissue surface temperature is cooler than the underlying collagen tissue, (iii) conditions in which a standard thermal gradient is reduced or equalized in temperature between the tissue surface and the underlying collagen, or (iv) monitoring the heat content (temperature and exposure duration) of the tissue surface to avoid blistering during treatment, regardless of the tissue surface temperature relative to the underlying collagen tissue.

Transcutaneously means that the delivery device delivers electromagnetic energy directly through the tissue surface.

Percutaneously means that the delivery device is inserted through the skin or the tissue surface through an endoscope, arthroscope, and the like.

Transmucosal means that the delivery device delivers electromagnetic energy directly through the mucosal surface.

Permucosal means that a delivery device is inserted through a mucosal surface through an endoscope, arthroscope, and the like.

A first degree burn means a burn that involves only the epidermis. It is characterized by erythema.

A second degree burn means a burn that destroys the epithelium and a variable portion of the dermis.

A third degree burn means a burn that destroys the entire thickness of skin, including the epithelium and dermis.

The present invention provides a method for forming and contracting scar collagen below a tissue surface in a selected tissue site. The formation or induction of scar collagen formation can be done transcutaneously, with a reverse thermal gradient, percutaneously, transmucosally, permucosally, or through a device including but not limited to an endoscope. An electromagnetic energy apparatus is provided and includes an electromagnetic energy source and a delivery device. The delivery device is positioned on the tissue surface. Electromagnetic energy is produced from the electromagnetic energy source and delivered through the tissue surface to the selected tissue site for a sufficient time to induce scar collagen formation in the selected tissue site. No deeper than a second degree burn is formed on the tissue surface. The scar collagen is subsequently contracted. This method is particularly useful in soft tissue sites that are devoid or deficient in collagen.

In another embodiment, a method is disclosed for forming callus deposition in a selected periosteum tissue site. An electromagnetic energy apparatus is provided and includes an electromagnetic energy source and a delivery device. The delivery device is positioned on a tissue surface of the selected periosteum tissue site. Electromagnetic energy is produced from the electromagnetic energy source. Electromagnetic energy is delivered from the delivery device, through the tissue surface, and to the selected periosteum tissue site for a sufficient time to induce callus formation in the selected periosteum tissue site. The callus is subsequently contracted. The method for forming callus can be done transcutaneously, with a reverse thermal gradient, percutaneously, transmucosally permucosally, or through a device including but not limited to an endoscope.

The methods of the present invention use an electromagnetic energy source to apply electromagnetic energy to a selected tissue site. The electromagnetic energy can be delivered transcutaneously, with a reverse thermal gradient, percutaneously, transmucosally, permucosally, or through a device including but not limited to an endoscope. The electromagnetic energy induces scar collagen formation in tissue sites that, (i) have pre-existing collagen, (ii) are deficient in pre-existing collagen, or (iii) lack pre-existing collagen. Following the formation of the scar collagen, the application of electromagnetic energy contracts the scar collagen.

Additionally, the methods of the present invention provide for the contraction of collagen tissue underlying a tissue surface area. The overlying layer of tissue is not ablated. No deeper than a second degree burn is produced in the overlying layer of tissue, and preferably no deeper than a first degree burn.

Suitable applications for the methods of the present invention include but are not limited to, tightening and firming soft tissue, treatment of unstable joints due to collateral ligament laxity, the treatment of unstable spinal column disorders, treatment of weaknesses of the abdominal wall, treatment of other connective tissues, esophageal hernia with reflux, urinary incontinence in women, dysdynamic segments of the myrocardium and other aneurysmal dilatations of the vessels, sleep apnea, laxity and wrinkling of the skin, and the like.

Laxity and wrinkling of the skin occurs as a consequence of inadequate support of the epidermis. The induction of scar collagen deposition is used for the treatment of wrinkles. Improved skin turgor is accomplished by first replenishing the collagen matrix that has been lost with aging. Following the deposition of nascent scar collagen in the dermis, contraction of collagen with a reverse thermal gradient corrects the laxity and wrinkling of the skin without resorting to resurfacing techniques that require the application of a standard thermal gradient burn to the skin. This is achieved without undergoing a lengthy post-operative healing process. Bleeding and infection are reduced. Second degree burns to the superficial skin are minimized. The melanocytes are not damaged and pigmentary irregularities are avoided.

In one embodiment, skin tightening with a reverse thermal gradient contraction of collagen corrects areas such as the thighs, knees, arms, back, face and neck lifts, and hips without unsightly scarring. Elastosis, or stretching of the abdominal skin from pregnancy is corrected without the long scar commonly associated with an abdominoplasty. Breast uplifts, i.e., mastoplexies, no longer require extensive incisions.

Thermal remodeling of collagen can occur with both native (dermal) collagen and collagen produced as part of the healing process. Wound healing involves an initial inflammatory stage that is followed by a period of rapid nascent collagen production that morphologically appears as a scar. The biophysical properties of collagen are the same regardless of its origin.

One apparatus used to create the reverse thermal gradient is a composite heating pad that has both cooling elements and electromagnetic delivery devices. The heating pad is configured to the topography of the treatment area and is incorporated into an elastic garment. Partial denaturization of collagen is achieved with each treatment. Thermal transducers measure the surface temperature of the treatment area to avoid blistering. In one embodiment the deeper dermis is heated to above 65 degrees for collagen contraction. Sequential treatments are designed to allow for more precision of the end result. Areas of application are not confined by requirements to either hide surgical incisions or transition along aesthetic boundaries.

Various types of electromagnetic energy can be utilized with the present invention. Electromagnetic energy may be any kind that can cause cell heating or physical destruction by being applied to collagen tissue. Examples of suitable electromagnetic energy sources include, but are not limited to RF, microwave, ultrasound, laser and the like.

Referring now to FIG. 1, an apparatus 10 applies electromagnetic energy through a skin layer 12, such as the epidermis, and to the underlying collagen tissue 14 without substantially modifying melanocytes and other epithelial cells 16 found in the lower layer of epidermis layer 12.

A porous membrane 18 is adapted to receive an electrolytic solution 20. Porous membrane 18 becomes inflated to substantially conform a contacting exterior surface 22 of porous membrane 18 which is in close thermal contact with epidermis 12. Porous membrane 18 includes a cooling lumen 24 for receiving a cooling fluid that imparts a cooling effect on epidermis layer 12.

One or more electromagnetic electrodes 26 are positioned at various places in porous membrane 18. In one embodiment, electromagnetic electrodes 26 are positioned on a side that is substantially opposing to contacting exterior surface 22. In other embodiments, electromagnetic electrodes 26 are placed closer to cooling lumen 24. In embodiment particularly suitable for the hips, porous membrane is about 20 cm by 30 cm, with an oval shape.

An electromagnetic power source 28 is coupled to electromagnetic electrodes 26 and a source of electrolytic solution 30 is coupled to porous membrane 18.

In one method of the present invention, collagen tissue in a dermis underlying the epidermis of the skin is transcutaneously contracted with the use of a thermal heating apparatus. Electromagnetic energy is transcutaneously delivered through the epidermis to the underlying dermis. Fibroblast proliferation is initiated in the underlying dermis. Scar collagen is formed in the underlying dermis. The scar collagen is subsequently contracted and the skin is tightened.

In another embodiment, a method is provided for contracting collagen tissue in a subcutaneous fat layer through an overlying epidermis layer. A thermal heating apparatus produces electromagnetic energy. The electromagnetic energy can be delivered transcutaneously, with a reverse thermal gradient, percutaneously, transmucosally permucosally, or through a device including but not limited to an endoscope. The electromagnetic energy is directed through the epidermis to the underlying subcutaneous fat layer. Fibroblast proliferation is initiated in the subcutaneous fat layer. Scar collagen is formed and then tightened.

Figure 2:
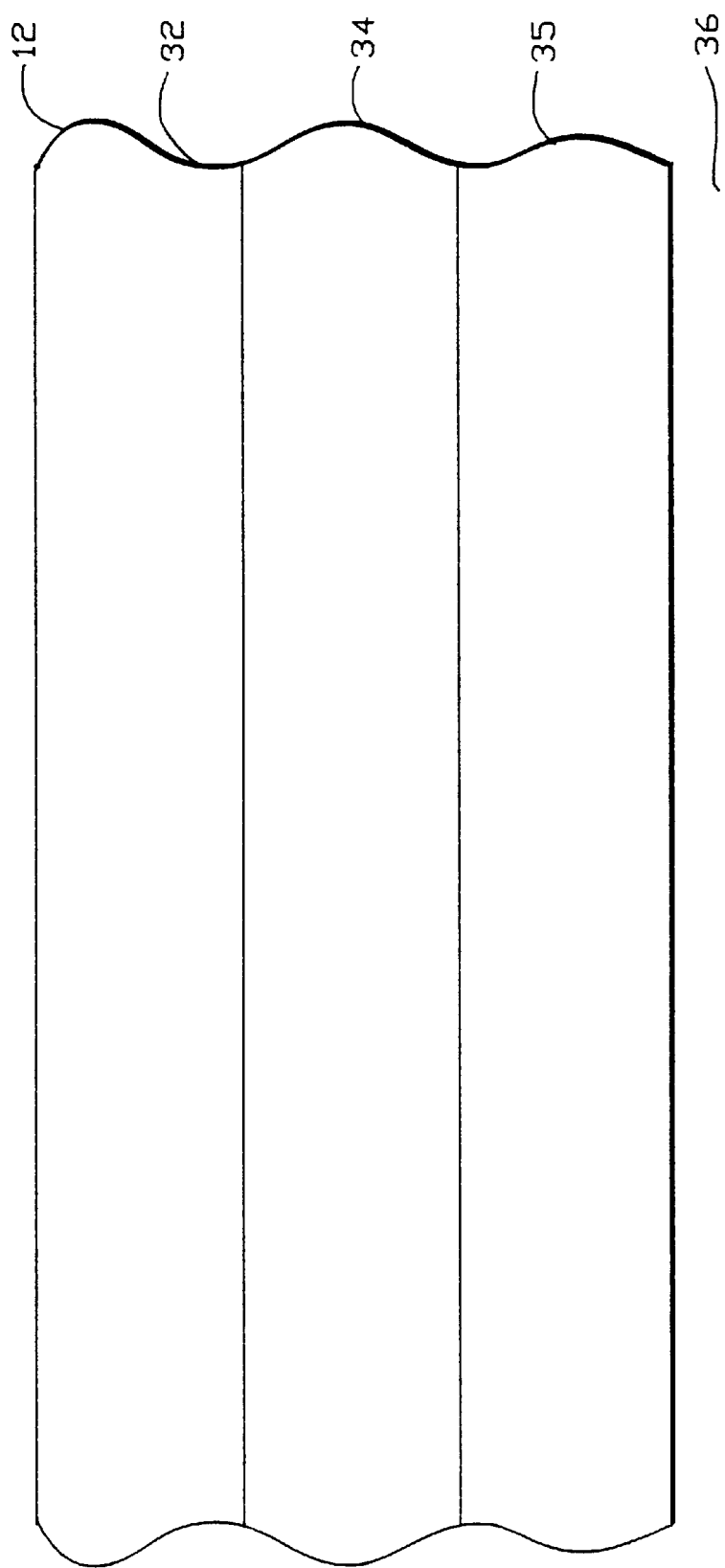
FIG. 2 is a cross-sectional view of the skin and underlying tissue.

With referenced now to FIG. 2, electromagnetic energy can be applied through epidermis layer 12, to papillary dermis layer 32, to reticular dermis layer 34, to subcutaneous layer 35, as well as to underlying soft tissue 36. The extent of collagen in the various layers is <5% in the epidermis, ~50% in the dermis, ~20% in the subcutaneous, ~10% in the muscle with overlying fascia. Shrinking of collagen tissue takes place in a direction parallel to the axis of the collagen fibers. Thermal shrinkage of collagen begins with the denaturization of the triple helix structure of the collagen fibers. This occurs when electromagnetic energy is applied to the collagen tissue causing the hydrolysis of heat labile cross links of the collagen network.

Figure 3:
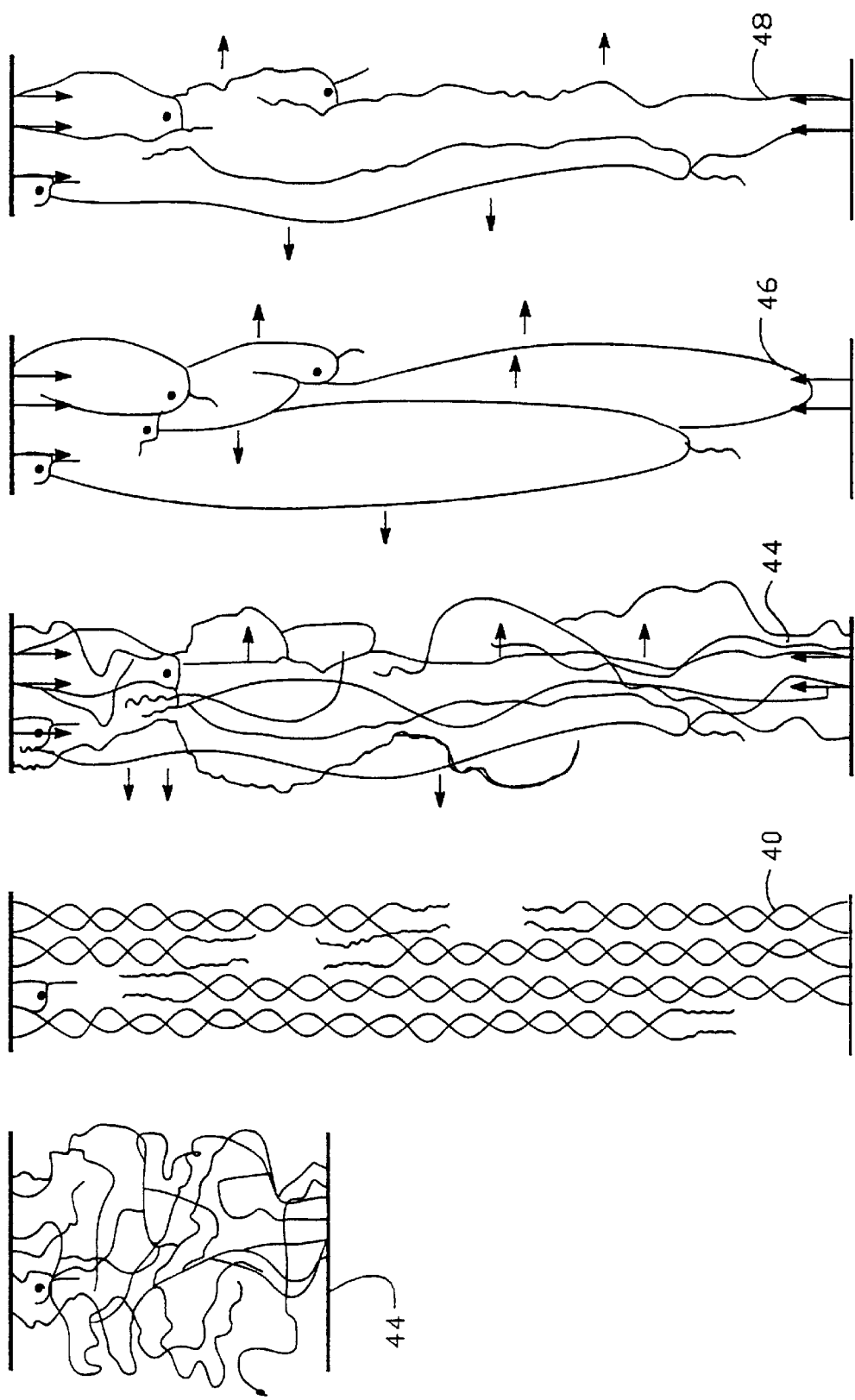
FIG. 3 is a schematic representation of the collagen network.

FIG. 3 is a schematic representation of a collagen network behavior under the influence of heat. The thickened lines represent the chains originally bound by covalent cross links. The arrows indicate tensions exerted on the collagen chains by the effect of heat. More particularly, FIG. 3 illustrates (i). native collagen network 40, (ii). collagen 42 under isometric conditions, (iii). collagen network without any restraint, (iv). collagen network 46 under isometric tension as long as the nodes are stable, and (v). collagen network 48 under isometric tension after some cross links have been cleaved.

Electromagnetic electrodes 26 can be RF electrodes comprising a single electrode, or a plurality which can form a segmented flexible circuit. Electromagnetic power source 28 is then an RF generator. Electrolytic solution 20 is introduced into porous membrane 18 and passes by RF electrodes 26. Electrolytic solution 20 transfers RF power from RF electrodes 28 to the desired underlying collagen tissue to achieve partial denaturization of the collagen molecule.

Generally, RF electrodes 26 can be monopolar or bipolar. In the monopolar mode, RF current flows through body tissue from a return electrode which can be in a form of a conductive pad applied to the patients outer skin. Maximum heating occurs where the current density is the greatest.

During a treatment phase, the denaturization of collagen molecules can be conducted under feedback control. Treatment can occur without the attention of medical supervision. Feedback is accomplished by (i). visualization, (ii). impedance, (iii). ultrasound, or (iv). temperature measurement. Optionally included and preferably positioned on contacting exterior surface 22 can be one ore more thermal sensors 52, as well as one or more impedance monitors 54. Thermal sensors 52 permit accurate determination of the surface temperature of epidermis layer 12.

Electrolytic solution 20 can be preheated to a selected temperature and modified as necessary. This reduces the amount of time needed to effect at satisfactory denaturization of collagen molecules and subsequent skin tightening.

Porous membrane 18 can be made of a material that is an insulator. For purposes of this disclosures, an insulator is a barrier to thermal or electrical energy flow. Porous membrane 18 can be made of a material which permits controlled delivery of electrolytic solution 20 to epidermis layer 12. Porous membrane 18 can be made of a variety of materials including, but not limited to knitted polyester, continuous filament polyester, polyester-cellulose, rayon, polyamide, polyurethane, polyethylene and the like. Suitable commercial products include, (i). Opcell available from Centinal Products Corp., Hyannis, Mass., and (ii). UltraSorb, HC 4201 or HT 4644 MD from Wilshire Contamination Control, Carlsbad, Calif. Pockets or zones 56 can be formed around RF electrodes 26. Each pocket 56 has a lower porosity for the flow of electrolytic solution 20 than all other sections of porous membrane 18. Differences in porosity can be achieved with different types of materials which form porous membrane 18. Electrolytic solution 20 is retained in pockets 56 longer than in non-pocket sections of porous membrane 18, and there is a greater transfer of RF energy to electrolytic solution 20, creating a larger electrode. The larger electrode produces RF and thermal energy to create a larger electrode effect. However, this does not effect the creation of the reverse thermal gradient. RF energy is still transferred through porous membrane 18 passing in the vicinity of cooling lumen 24, in order to create a lower temperature at epidermis layer 12 and the temperature increases as deeper layers are reached.

In a skin contracting method of the present invention, a tighter, more youthful skin envelope is achieved. This is accomplished without undergoing a lengthy post-operative healing process. Bleeding and infection is reduced. Second degree burns to the superficial skin are minimized. The melanocytes are not damaged and pigmentary irregularities are avoided.

Because scarring and pigmentary irregularities are avoided, skin or other tightening occurs in areas previously considered "off-limits" to standard methods of surgical resection, laser and chemical resurfacing. Skin tightening with a reverse thermal gradient contraction of collagen can correct areas including but not limited to the thighs, knees, arms, back and hips without unsightly scarring of standard techniques. In addition, areas previously corrected by aesthetic procedures, such as face and neck lifts, can be corrected without requiring surgery or the typical incisions around the ear. Elastosis or stretching of the abdominal skin from pregnancy can be corrected without the extensive incision of an abdominoplasty. The method of the present invention can also be used for mastopexies or breast uplifts.

The fibrous septae in subcutaneous fat layers can be contracted to tighten the soft tissue. Along with these extracellular effects of collagen, intracellular thermal induction effects upon the fat cell or lipocyte results in a net egress of fat from the lipocyte which achieves a net reduction of volume of the treated area. A second thermal device is used in tandem with the initial thermal device to achieve liposculpture of the treated area. The second device can be designed with a convergent lens that is focused at the appropriate level on the subcutaneous tissue.

Figure 4:
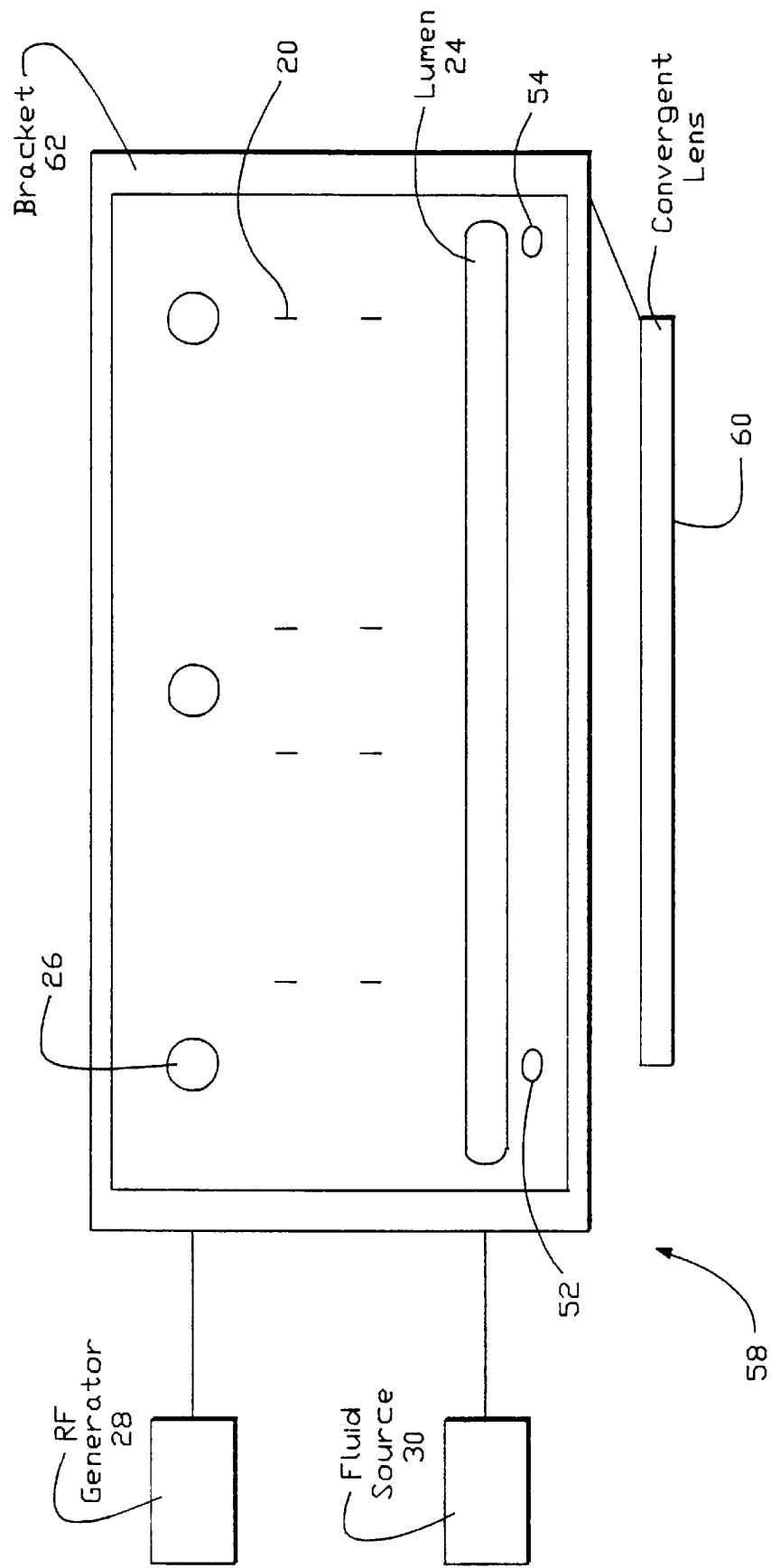
FIG. 4 is a schematic diagram of an apparatus for applying electromagnetic energy to underlying subcutaneous layers or deeper soft tissue layers to create a desired contour effect by partially denaturing collagen tissue, and without substantially modifying melanocytes and other epithelial cells in the epidermis.
Figure 5:
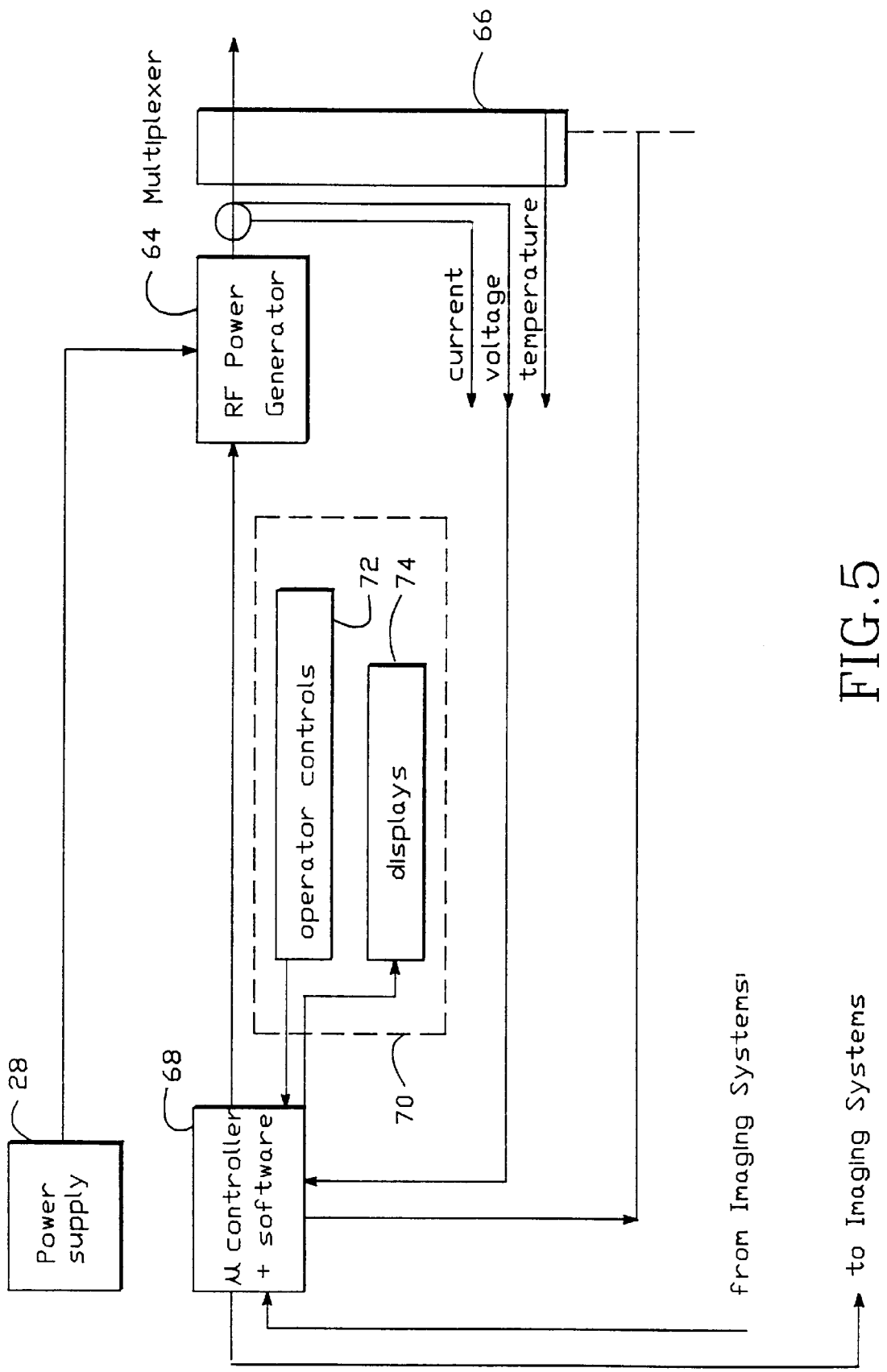
FIG. 5 is a block diagram of an RF system which can be utilized with the present invention.

Referring now to FIG. 4, an apparatus 58 for creating a desired contour effect of underlying subcutaneous layers or deeper soft tissue layers which include loculations of fat with fibrous septae made of collagen tissue is illustrated. The apparatus 58 of FIG. 4, includes a porous membrane 18, electrolytic solution 20, a contacting exterior surface 22, a cooling lumen, electromagnetic electrodes 26, an electromagnetic power source 28, an electrolytic solution source 30, one or more thermal sensors 52, as well as one or more impedance monitors 54. Apparatus 58 also includes a focussing element 60 which focuses electromagnetic energy from electrolytic solution 20 to the underlying collagen tissue. Focussing element 60 and electrolytic solution 20 create a reverse thermal gradient from epidermis layer 12 to the underlying collagen tissue 14. Focussing element 62 can be, in the case of ultrasonic energy, a lens having a flat planer surface on the radiation wave incident side and a concave exit face, see *Ultrasonics Theory and Application,* by G. L. Goberman, Heart Publishing Co., New York (1959), at section 2.6. The use of such a focussing lens for ultrasonic energy with a planer wave receiving face and concave exit face is also described in the article "Deep Local Hyperthermia for Cancer Therapy: Extreme Electromagnetic and Ultrasound Technics," A. Y. Cheung and A. Neyzari, *Cancer Research,* Vol. 44, pp. 4736–4744, October 1984.

Radio frequencies can be the electromagnetic energy source, and various localizing technique, well known in the art, can be utilized. In one embodiment, radio frequency energy is supplied by capacitive coupling directly to epidermis layer 12 for areas close to the dermal tissue. Radio frequency induction focussing can be achieved with the use of plural focussing coils which are adaptive at the zone of interest and are elsewhere subtractive. Alternatively, radio frequency energy may be focused by having a multiple beam phased array. For concave focussing see, "Tumor reduction by radio frequency therapy response", H. H. Lavien et al., *JAMA,* Vol. 233, at 2198–2200.

Alternative radio frequency focussing methods are disclosed in "Equipment for Local Hyperthermia Therapy of Cancer", C. F. Babbs et al., *Medical Instrumentation,* Vol. 16, No. 5, September–October 1982, pp. 245–248.

It will be appreciated that focussing element 60 can be a convergent lens. Further, focussing element 60 can be positioned in porous membrane 18, and at the exterior 16 between epidermis layer 12 and porous membrane 18. Further, a coupling device 62 can be included which couples focussing element 60 with porous membrane 18. In one embodiment, coupling device 62 is a bracket which is positioned around a periphery of porous membrane 18, and supports focussing element 50 in relation to porous membrane 18.

In the method for tightening skin, porous membrane 18 and thermal energy source 26 are provided. A reverse thermal gradient is created which cools a surface of epidermis layer 12 while heating underlying collagen containing layers. Epidermis layer 12 as well as underlying collagen containing tissue are heated, without substantially effecting the melanocytes and other epithelial cells in epidermis layer 12, resulting in a denaturization of collagen molecules, causing a contraction of the collagen tissue and a tightening of the skin. This method can be applied numerous times. In many instances, it may be desirable to tighten the skin to a certain level and then in subsequent treatments the skin is tightened further. There may be four fine treatments to fine tune the contour effects with greater precision. In this method, collagen containing tissue is partial denatured and fat cell destruction is minimized. This is achieved by partially denaturing by cleaving heat labile cross links of the collagen molecules.

The reverse thermal gradient provides a variation in temperature throughout the various tissue layers. For example, in various embodiments, the reverse thermal gradient has a tissue surface temperature range from about 40 to 60 degrees C., and a selected underlying tissue site temperature, i.e., where scar collagen is formed or where collagen is contracted, of about 60 to 80 degrees C. In other embodiments, when the reverse thermal gradient is a diminished or equalized standard thermal gradient the temperature ranges can be much broader.

In another embodiment, a method for liposculpturing an area of the body where there is an underlying area comprised of a loculation of fat that has collagen tissue as a fibrous septae also includes creating a reverse thermal gradient from epidermis layer 12 to the desired underlying loculation of fat layer. Sufficient electromagnetic energy is supplied through epidermis layer 12, without damaging or substantially modifying the melanocytes and other epithelial cells, through other skin layers and is focused on the collagen tissue of the fibrous septae. Electromagnetic energy partially denatures the collagen tissue with a minimal destruction of fat cells. Again, this is achieved by partially denaturizing, e.g., by cleaving, heat labial cross links of collagen molecules. The reverse thermal gradient produces a net mobilization of intracellular fat with diminished destruction of fat cells.

In yet another embodiment of the invention, thermal induction of osteoblasts in the periosteum results in callus (calcium matrix) deposition. Callus contains a higher percentage of collagen than mature bone and subsequent remodeling with thermal contraction is possible. Maturation of the remodelled callus with calcium deposition results in stable bony fusion of treated areas.

Without limitation, power source 28 can be an RF source. RF power source 28 feeds energy to an RF power generator 64 and then to RF electrodes 26. A multiplexer 66 measures current, voltage and temperature, at the numerous thermal sensors associated with to each RF electrode 26. RF electrodes 26 can be individually measured. Multiplexer 66 is driven by a controller 68 which can be a digital or analog controller, or a computer with software. When controller 68 is a computer it can include a CPU coupled through a system bus. On the system can be a keyboard, disk drive, or other non volatile memory systems, a display, and other peripherals, as are well known in the art. Also coupled to the bus are a program memory and a data memory.

An operator interface 70 includes operator controls 72 and a display 74. Controller 68 can be coupled to different types of imaging systems including ultrasonic, thermal sensors 52, and impedance monitors 54.

Current and voltage are used to calculate impedance. A diagnostic phase can be initially run to determine the level of treatment activity. This can be done through ultrasound as well as other means. Diagnostics can be performed both before and after treatment.

Thermal sensors 52, and thermal sensors 76 contained within RF generator 64 measure voltage and current that is delivered to the desired treatment site. The output for these sensors is used by controller 68 to control the delivery of RF power. Controller 68 can also control temperature and power. An operator set level of power and/or temperature may be determined and this will not be exceeded. Controller 68 maintains the set level under changing conditions. The amount of RF energy delivered controls the amount of power. A profile of power delivered can be incorporated in controller 68, as well as a preset amount of energy to be delivered. Feedback can be the measurement of impedance, temperature, or other indicators and occurs either at control 68 or at RF generator 64, if it incorporates a controller. For impedance measurement, this can be achieved by supplying a small amount of non therapeutic RF energy. Voltage and current are then measured to confirm electrical contact.

Circuitry, software and feedback to controller 68 result in full process control and are used to change, (i). power, (ii). the duty cycle, (iii). monopolar or bipolar energy delivery, (iv). electrolytic solution 20 delivery, flow rate and pressure and (v). can determine when the process is completed through time, temperature and/or impedance. These process variables can be controlled and varied based upon tissue temperature monitored at multiple sites on contacting exterior surface 22 as well as monitoring impedance to current flow at each RF electrode 26, indicating changes in current carrying capability of the tissue during the process. Further, controller 68 can provide multiplexing, monitor circuit continuity, and determine which RF electrode 26 is activated.

Figure 6:
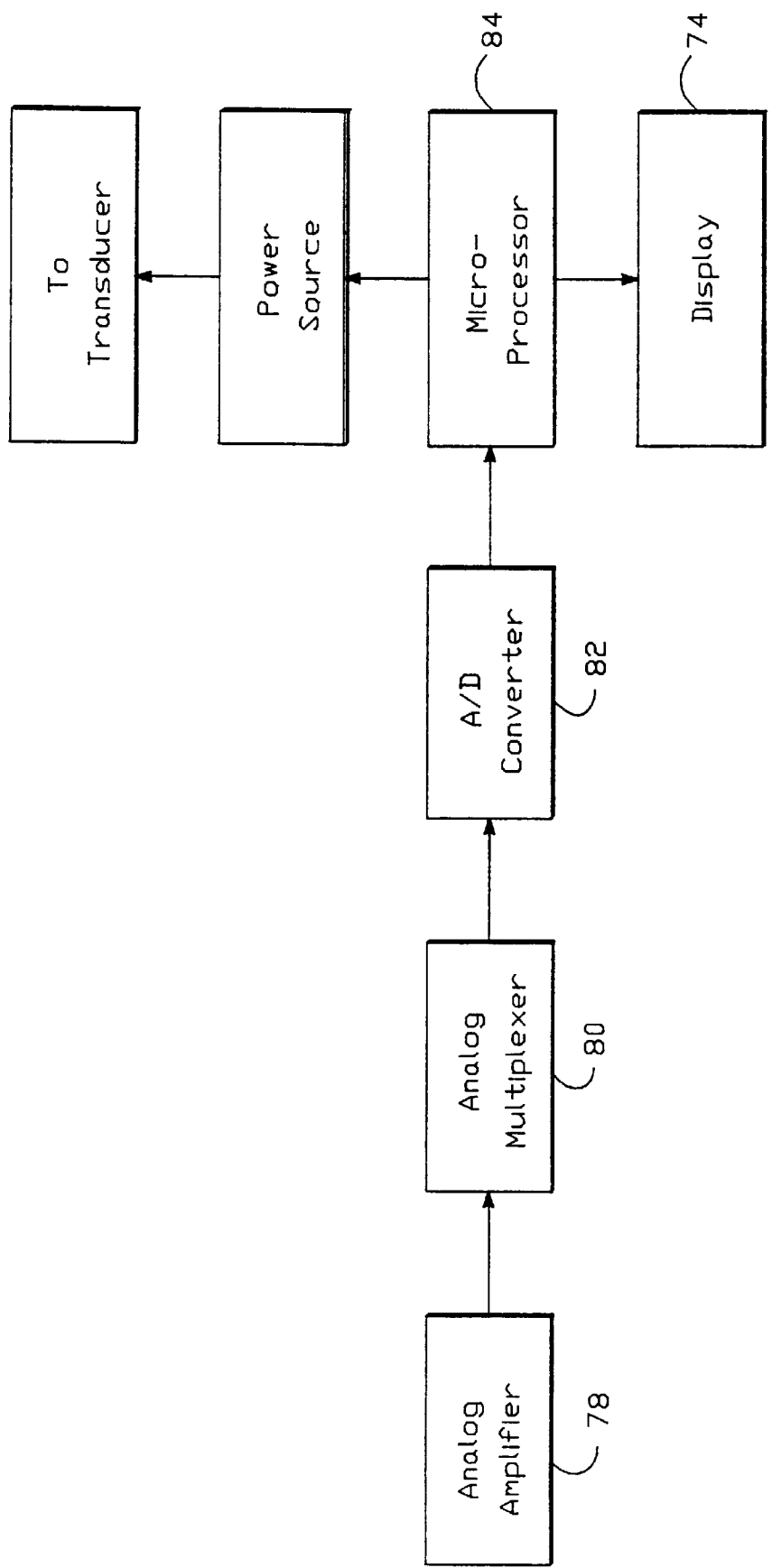
FIG. 6 is a block diagram of processing circuit of one embodiment of the invention.

A block diagram of one embodiment of suitable processing circuitry is shown in FIG. 6. Thermal sensors 52 can be thermistors which have a resistance that varies with temperature. Analog amplifier 78 can be a conventional differential amplifier circuit for use with thermistors and transducers. The output of analog amplifier is sequentially connected by an analog multiplexer 80 to the input of an analog digital converter 82. The output of amplifier 78 is a voltage which represents the respective sensed temperatures. The digitized amplifier output voltages are supplied by analog to digital converter 82 to a microprocessor 84. Microprocessor 84 calculates the temperature or impedance of the tissue. Microprocessor 84 can be a type 6800. However, it will be appreciated that any suitable microprocessor or general purpose digital or analog computer can be used to calculate impedance or temperature.

Microprocessor 84 sequentially receives and stores digital representations of impedance and temperature. Each digital value received by microprocessor 84 corresponds to different temperatures and impedances.

Calculated temperature and impedance values can be indicated on display 74. Alternatively, or in addition to the numerical indication of temperature or impedance, calculated impedance or temperature values can be compared by microprocessor 84 with temperature and impedance limits. When the values exceed predetermined temperature or impedance values a warning can be given on display 74 and additionally, the delivery of RF energy to its respective electrode can be decreased or multiplexed to another electrode. A control signal from microprocessor 84 can reduce the power level by RF generator 64, or de-energize the power delivered to any particular electrode. Controller 68 receives and stores the digital values which represent temperatures and impedances sent. Calculated surface temperatures and impedances can be forwarded by controller 68 to display 74. If desired, the calculated surface temperature of epidermis layer 12 is compared with a temperature limit and a warning signal can be sent to display 74. Similarly, a control signal can be sent to RF power source 26 when temperature or impedance values exceed a predetermined level.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. A method for inducing the formation of scar collagen in a selected collagen containing tissue site beneath an epidermis skin surface, comprising:

providing an energy source;

producing energy from the energy source;

creating a reverse thermal gradient through the skin epidermis surface where a temperature of the skin epidermis surface is lower than the selected collagen containing tissue site; and delivering energy from the energy source through the skin epidermis surface to the selected collagen containing tissue site for a sufficient time to induce collagen formation in the selected collagen containing tissue site, minimizing cellular necrosis of the skin epidermis surface and tightening the skin epidermis surface.

2. The method of claim 1, wherein the energy is transcutaneously delivered to the selected collagen containing tissue site.

3. The method of claim 1, wherein the energy is percutaneously delivered to the selected collagen containing tissue site.

4. The method of claim 1, wherein the energy is transmucosally delivered to the selected collagen containing site.

5. The method of claim 1, wherein the energy is permucosally delivered to the selected collagen containing tissue site.

6. The method of claim 1, wherein the energy is transcutaneously delivered to the selected collagen containing tissue site for a sufficient time to induce collagen formation in the selected collagen containing tissue site with no deeper than a first degree burn formed on the skin surface.

7. The method of claim 1, wherein the energy is transcutaneously delivered to the selected collagen containing tissue site for a sufficient time to induce collagen formation in the selected collagen containing tissue site with no deeper than a second degree burn formed on the skin epidermis surface.

8. The method of claim 1, wherein a combination of an amount of energy delivered to the tissue surface and to the selected collagen containing tissue site creates a reverse thermal gradient through the skin epidermis surface to the selected collagen containing tissue site.

9. The method of claim 1, wherein the energy source is an RF source.

10. The method of claim 1, wherein the energy source is a microwave source.

11. The method of claim 1, wherein the energy source is a short wave source.

12. The method of claim 1, wherein the selected collagen containing tissue site is heated to a temperature range of 40 to 60 degrees C.

13. The method of claim 1, wherein the selected collagen containing tissue site is heated to a temperature of 60 to 80 degrees or greater.

14. The method of claim 1, wherein the selected collagen containing tissue site comprises soft tissue.

15. The method of claim 1, wherein the formation of the collagen alters a consistency of the selected collagen containing tissue site.

16. The method of claim 1, wherein the formation of the collagen changes the geometry of the selected collagen containing tissue site.

17. A method for inducing the formation of scar collagen in a selected collagen containing tissue site beneath an epidermis skin surface, comprising:

providing an energy source with an energy delivery surface;

positioning the energy delivery surface on the epidermis skin surface;

creating a reverse thermal gradient through the epidermis skin surface sufficiently to induce a formation of new collagen in the selected collagen containing tissue site with no deeper than a second degree burn created on the skin epidermis surface, wherein a temperature of the skin epidermis surface is lower than the collagen containing tissue site;

contracting at least a portion of the new collagen; and tightening the epidermis skin surface.

18. The method of claim 17, wherein the energy is transcutaneously delivered to the selected collagen containing tissue site.

19. The method of claim 17, wherein the energy source is an RF source.

20. A method for inducing the formation of scar collagen in a selected collagen containing tissue site beneath an epidermis skin surface, comprising:

providing an energy source;

producing energy from the energy source;

delivering energy from the energy source through the skin epidermis surface to the selected collagen containing tissue site for a sufficient time to induce a formation of new collagen in the selected collagen containing tissue site with no deeper than a second degree burn created on the skin epidermis surface;

minimizing destruction of fat cells underlying the skin epidermis surface;

contracting at least a portion of the new collagen; and modifying the epidermal skin surface.

21. The method of claim 20, wherein the energy is transcutaneously delivered to the selected collagen containing tissue site.

22. The method of claim 20, further comprising:

creating a reverse thermal gradient through the skin epidermis surface where a temperature of the skin epidermis surface is lower than the selected collagen containing tissue site.

23. The method of claim 20, wherein the energy source is an RF source.

* * * * *

UNITED STATES PATENT AND TRADEMARK OFFICE
CERTIFICATE OF CORRECTION

PATENT NO. : 6,241,753 C1  Page 1 of 1
APPLICATION NO. : 90/010166
DATED : February 9, 2010
INVENTOR(S) : Edward W. Knowlton It is certified that error appears in the above-identified patent and that said Letters Patent is hereby corrected as shown below:

In the Assignee section on the cover page, change "General Electric Capital Corporation, Danbury, CT" to --Thermage, Inc., Hayward, CA--.

Signed and Sealed this

Thirteenth Day of April, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 6,241,753 C1 | Page 1 of 1 |
| APPLICATION NO. | : 90/010166 | |
| DATED | : February 9, 2010 | |
| INVENTOR(S) | : Knowlton | |

It is certified that error appears in the above-identified patent and that said Letters Patent is hereby corrected as shown below:

Col. 2, line 19, after "degrees", add --C--.

Signed and Sealed this
Fifteenth Day of March, 2011

David J. Kappos
*Director of the United States Patent and Trademark Office*

US006241753C1

(12) EX PARTE REEXAMINATION CERTIFICATE (7354th)
United States Patent
Knowlton

(10) Number: US 6,241,753 C1
(45) Certificate Issued: *Feb. 9, 2010

(54) METHOD FOR SCAR COLLAGEN FORMATION AND CONTRACTION

(75) Inventor: Edward W. Knowlton, Danville, CA (US)

(73) Assignee: General Electric Capital Corporation, Danbury, CT (US)

Reexamination Request:
No. 90/010,166, May 15, 2008

Reexamination Certificate for:
Patent No.: 6,241,753
Issued: Jun. 5, 2001
Appl. No.: 08/583,815
Filed: Jan. 5, 1996

(*) Notice: This patent is subject to a terminal disclaimer.

Related U.S. Application Data

(63) Continuation-in-part of application No. 08/435,822, filed on May 5, 1995, now Pat. No. 5,755,753.

(51) Int. Cl.
*A61F 07/00* (2006.01)

(52) U.S. Cl. .............................. 607/99; 128/898; 607/96; 607/98; 607/100; 607/101; 607/102; 607/103; 607/104; 607/105; 600/21; 600/22; 600/23; 600/24

(58) Field of Classification Search ........................ None
See application file for complete search history.

(56) References Cited

U.S. PATENT DOCUMENTS

| 4,140,130 | A | | 2/1979 | Storm, III |
| 5,458,596 | A | | 10/1995 | Lax et al. |
| 5,484,432 | A | | 1/1996 | Sand |
| 5,507,790 | A | | 4/1996 | Weiss |
| 5,755,753 | A | * | 5/1998 | Knowlton ..................... 607/98 |
| 6,405,090 | B1 | * | 6/2002 | Knowlton ................... 607/102 |
| 6,413,255 | B1 | | 7/2002 | Stern |

| 2002/0151887 | A1 | 10/2002 | Stern et al. |

FOREIGN PATENT DOCUMENTS

| CA | 1228401 | | 10/1987 |
| JP | 02-201315 | | 7/1990 |
| JP | 9503689 | | 4/1997 |
| WO | 9510326 | A1 | 4/1995 |

OTHER PUBLICATIONS

H. H. Leveen et al., "Tumor Eradication by Radiofrequency Therapy," *JAMA*, vol. 235, No. 20 at 2199 (May 17, 1976).

A.Y. Cheung and A. Neyzari, "Deep Local Hyperthermia for Cancer Therapy: External Electromagnetic and Ultrasound Techniques," *Cancer Research* (Suppl.), vol. 44 at 4738s (Oct. 1984).

C.F. Babbs et al., "Equipment for local hyterthermia therapy of cancer," *Medical Instrumentation*, vol. 16, No. 5, Sep.–Oct. 1982.

Chen et al., "Effects of All–Trans Retinoic Acid on UVB–Irradiated and Non–Irradiated Hairless Mouse Skin," *J. Invest. Dermatol* 98:248–254, 1992.

Christopher E.M. Griffiths, et al. "Restoration of Collagen Formation in Photodamaged Human Skin by Treitinoin (Retinoic Acid)," *New England J. Med.*, 329: 535–35 (Aug. 19, 1993).

(Continued)

*Primary Examiner*—Glenn K. Dawson

(57) ABSTRACT

A method is disclosed for forming and contracting scar collagen below a tissue surface in a selected tissue site. An electromagnetic energy apparatus is provided and includes an electromagnetic energy source and a delivery device. The delivery device is positioned on the tissue surface. Electromagnetic energy is produced from the electromagnetic energy source and delivered through the tissue surface to the selected tissue site for a sufficient time to induce scar collagen formation in the selected tissue site. No more than a second degree burn is formed on the tissue surface. The scar collagen is then contracted. This method is particularly useful in tissue sites that are devoid or deficient in collagen.

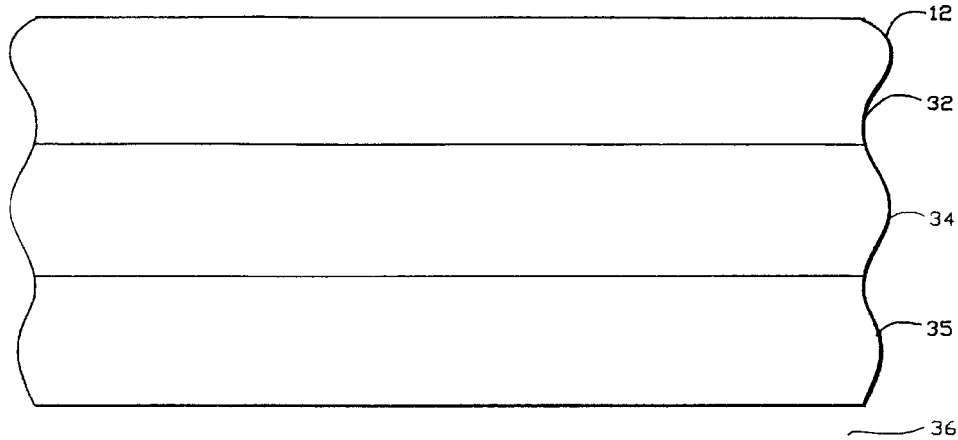

OTHER PUBLICATIONS

Ilaria Ghersetich, "Ultrastructural Study of Hyaluronic Acid Before and After the Use of a Pulsed Electromagnetic Field, Electrorydesis, in the Treatment of Wrinkles," *Int'l J. Dermatol.*, 33:661–663 (1994).

Dale P Devore, Elizabeth Hughes & Joy B. Scott, "Effectiveness of injectable filler materials for smoothing wrinkle lines and depressed scars," *Med. Prog. Tech.* 20:243–250 (1994).

Thermage's Second Supplemental Responses to Plaintiffs' First Set of Interrogatories, Second Supplemental Response to Interrogatory No. 1, *Alma Lasers, Inc.* v. *Thermage Inc.*. C.A. No. 07–224–GMS–MPT (Jan. 17, 2008).

Japanese Patent Office, translation of Official Action dated Jul. 17, 2009 in related Japanese Patent Application 2006–509276.

Cohen, et al., "Temperature Controlled Burn Generation System Based on a CO2 Laser and a Silver Halide Fiber Optic Radiometer", Lasers in Surgery and Medicine 32:413–416 (2003).

Kelly, et al., "Cryogen Spray Cooling in Combination with Nonablative Laser Treatment of Facial Rhytides", Arch Dermatol vol. 135, Jun. 1999 pp. 691–694.

Treede, et al., "Evidence for Two Different Heat Transduction Mechanisms in Nociceptive Primary Afferents Innervating Monkey Skin," Journal of Physiology (1995) 483.3, pp. 747–758.

Verdugo, et al., "Quantitative Somatosensory Thermotest", Brain (1992) 115, 893–913.

Kita, Plastic Surgery Hypodermis, http://plasticsurgery.about.com/od/glossary/g/hypodermis.htm?1, retrieved from the internet May 15, 2009.

Cecil Textbook of Medicine edited by Goldman, et al., 21st ed., copyright 2000, published by W.B. Saunders Company, part XXVII "Skin Diseases", p. 2263.

http://en.wikipedia.org/wiki/Skin, retrieved from the internet May 14, 2009.

Gray, The 3 skin layers: epidermis, dermis, subcutaneous fat, http://www.pg.com/science/skincare/Skin_tws_10.htm, retrieved from the internet May 15, 2009.

* cited by examiner

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1, 2, 6–9, 11, 12, 14–23 is confirmed.

Claim 13 is determined to be patentable as amended.

Claims 3–5 and 10 were not reexamined.

13. [The method of claim 1] *A method for inducing the formation of scar collagen in a selected collagen containing tissue site beneath an epidermis skin surface, comprising:*

*providing an energy source;*

*producing energy from the energy source;*

*creating a reverse thermal gradient through the skin epidermis surface where a temperature of the skin epidermis surface is lower than the selected collagen containing tissue site; and*

*delivering energy from the energy source through the skin epidermis surface to the selected collagen containing tissue site for a sufficient time to induce collagen formation in the selected collagen containing tissue site, minimizing cellular necrosis of the skin epidermis surface and tightening the skin epidermis surface,* wherein the selected collagen containing tissue site is heated to a temperature of 60 to 80 degrees or greater.

* * * * *